US00PP27036P3

(12) United States Plant Patent
Ohde

(10) Patent No.: US PP27,036 P3
(45) Date of Patent: Aug. 9, 2016

(54) ***LIPPIA* PLANT NAMED 'ECOLOPIA1'**

(50) Latin Name: ***Lippia nodiflora*×*Lippia canescens***
Varietal Denomination: ECOLOPIA1

(71) Applicant: Masataka Ohde, Oyama (JP)

(72) Inventor: Masataka Ohde, Oyama (JP)

(73) Assignee: Kurapia, Inc., Beverly Hills, CA (US)

( * ) Notice: Subject to any disclaimer, the term of this patent is extended or adjusted under 35 U.S.C. 154(b) by 115 days.

(21) Appl. No.: 14/120,979

(22) Filed: Jul. 18, 2014

(65) Prior Publication Data

US 2016/0021807 P1 Jan. 21, 2016

(51) Int. Cl.
*A01H 5/02* (2006.01)

(52) U.S. Cl.
USPC ..... Plt./263.1

(58) Field of Classification Search
USPC ..... Plt./263.1, 226
See application file for complete search history.

*Primary Examiner* — Anne Grunberg
(74) *Attorney, Agent, or Firm* — Cassandra Bright

(57) ABSTRACT

A new and distinct *Lippia* cultivar named 'ECOLOPIA1' is disclosed, characterized by tolerance to humidity, cold and disease, tall height and large leaf size. The new variety is a *Lippia*, useful for a variety of horticultural purposes.

3 Drawing Sheets

Latin name of the genus and species: *Lippia nodiflora*× *Lippia canescens*.

Variety denomination: 'ECOLOPIA1'.

BACKGROUND OF THE INVENTION

The new *Lippia* cultivar is a product of a planned breeding program conducted by the inventor. Masataka, Ohde in Oyama, Japan. The objective of the breeding program was to produce new *Lippia* varieties for ornamental commercial applications. The cross resulting in this new variety was made during May 2008.

The seed parent is the patented variety referred to as *Lippia nodiflora* 'Campanga Verde', U.S. Plant Pat. No. 20,120. The pollen parent is an unnamed *Lippia canescens*. The new variety was discovered on Jul. 1, 2009 by the inventor in a group of seedlings resulting from the 2008 crossing, in a research greenhouse in Oyama, Japan.

Asexual reproduction of the new cultivar 'ECOLOPIA1' was first performed at a commercial greenhouse in Oyama, Japan by vegetative cuttings on Jun. 4, 2010. More than 3 generations have been reproduced by vegetative cuttings. Subsequently, propagation has also shown that the unique features of this cultivar are stable and reproduced true to type.

SUMMARY OF THE INVENTION

The cultivar 'ECOLOPIA1' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'ECOLOPIA1'. These characteristics in combination distinguish 'ECOLOPIA1' as a new and distinct *Lippia* cultivar:

1. Tolerance to cold temperature.
2. Tolerance to disease.
3. Tolerance to high humidity.

4. Above average height.
4. Above average leaf size.

PARENT COMPARISON

Plants of the new cultivar 'ECOLOPIA1' are similar to pollen parent in most horticultural characteristics. The new variety however differs in the following characteristics:

1. Longer internode length.
2. Leaves are longer.
3. Shorter plant height.
4. Significantly more cold tolerant.

Plants of the new cultivar 'ECOLOPIA1' are similar to the seed parent, in most horticultural characteristics. The new variety however differs in the following characteristics:

1. Taller plant height.
2. More tolerance for cold temperature. Under conditions with an average day temperature of 4.5 Celsius, the new variety maintains 70% of green color while 'Campagna Verde' maintains only 30% of green color.
3. Stronger tolerance to disease under high heat and high humidity conditions.
4. Larger leaf size.

COMMERCIAL COMPARISON

'ECOLOPIA1' can be compared to the unpatented, unnamed commercial *Lippia nodiflora*. Plants of *Lippia nodiflora* are similar to plants of 'ECOLOPIA1' in most horticultural characteristics. However 'ECOLOPIA1' differs from *Lippia nodiflora* in the following characteristics:

1. The new variety is observed sterile. The comparator produces many seeds.
2. Greater cold tolerance.

BRIEF DESCRIPTION OF THE PHOTOGRAPHS

The accompanying photograph in FIG. 1 illustrates in full color typical flowers and foliage of a plant of 'ECOLOPIA1' grown outdoors in Oyama, Japan.

Figure 1:
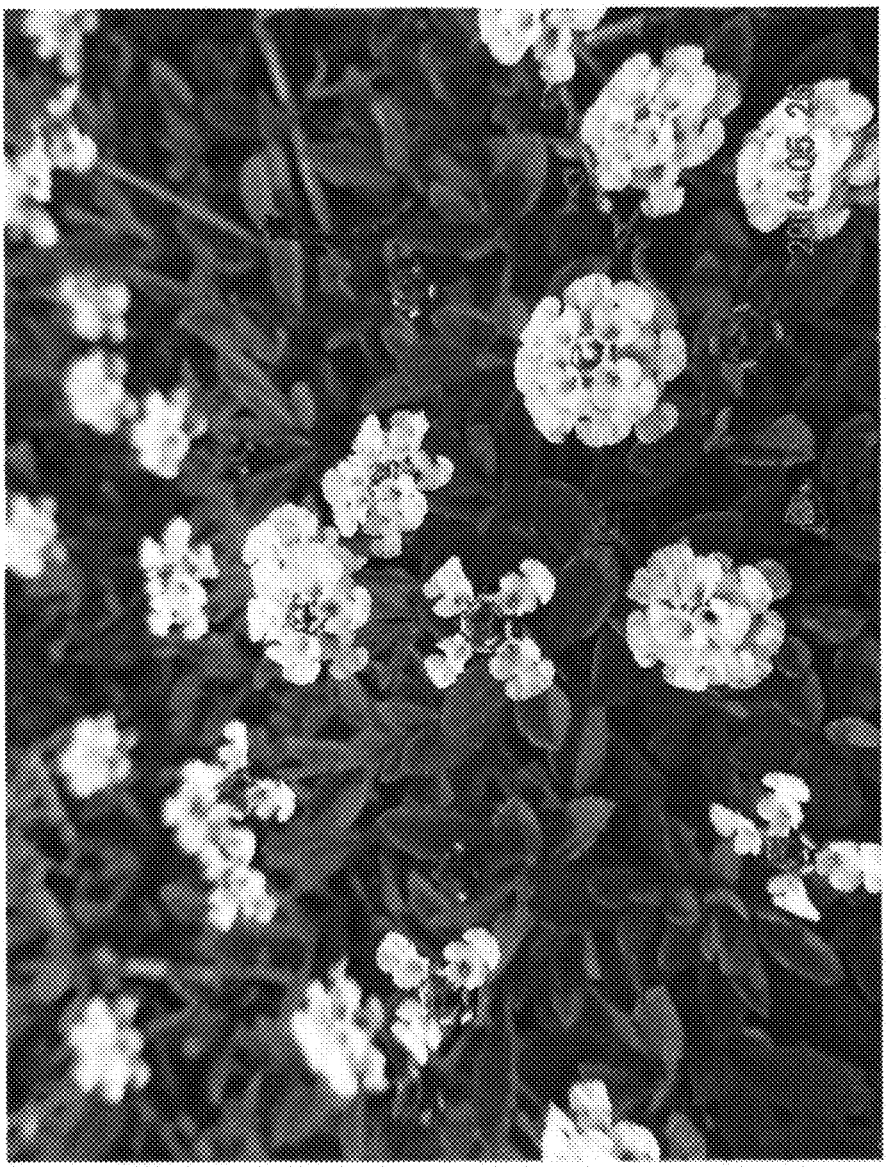
Figure 2:
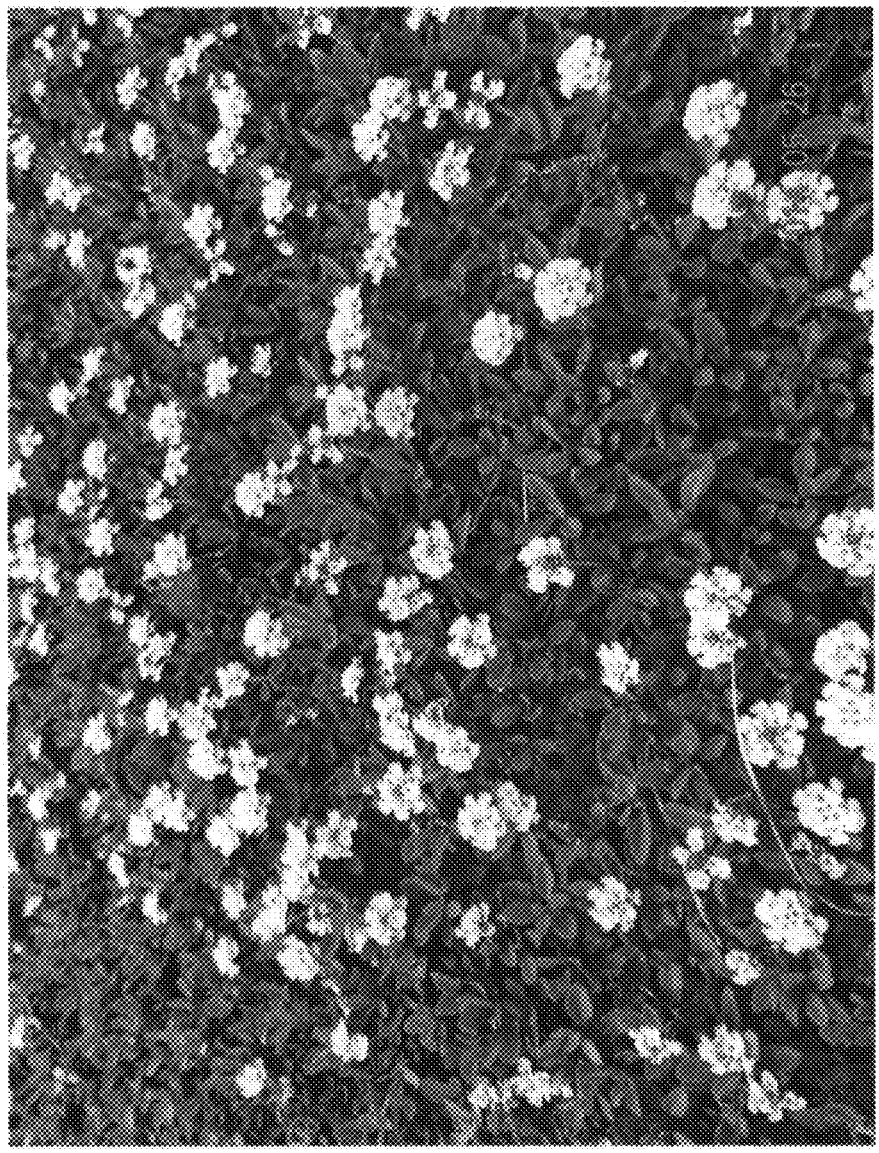
FIG. 2 illustrates a wider view of the plant.
Figure 3:
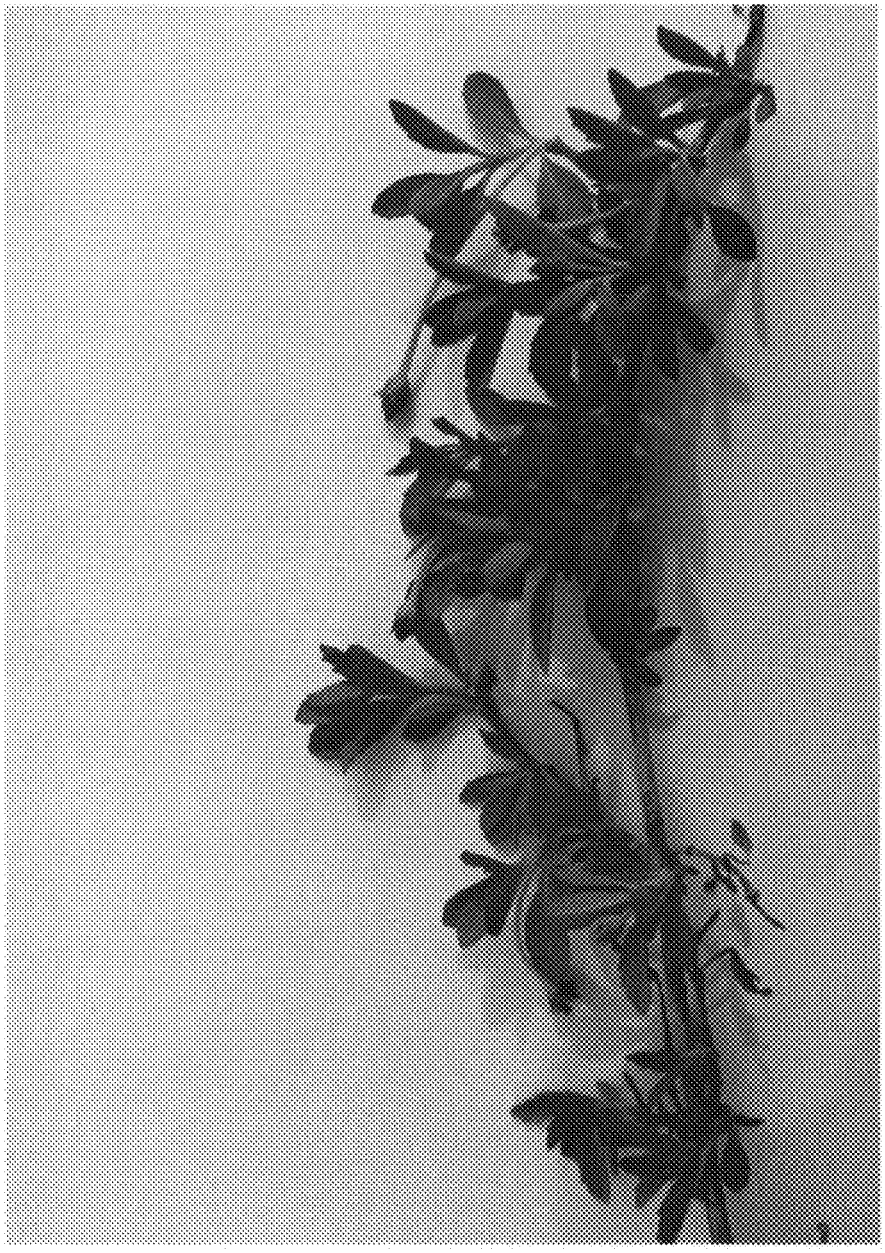
FIG. 3 illustrates a typical stem or "runner" of the new variety.

Plants are typically grown as ground over, the plants illustrated are planted directly in the ground. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007, except where general terms of ordinary dictionary significance are used. The following observations and measurements describe 'ECOLOPIA1' plants grown both outdoors and in a temperature controlled greenhouse in Oyama, Japan. Temperatures ranged from −7° C. to 25° C. at night to 3° C. to 50° C. during the day. No artificial light, photoperiodic treatments were given to the plants. Plants were grown both outside research field with plowed soil supplemented with fertilizer containing 8% N. 8% P, and 8% K, and in temperature-controlled and uncontrolled greenhouses in a mixture of Kanuma soil, peat and vermiculite supplemented with the same fertilizer. Measurements and numerical values represent averages of typical plant types.

Botanical classification: *Lippia nodiflora*×*Lippia canescens* 'ECOLOPIA1'.

PROPAGATION

Time to initiate roots: 3 to 7 days at approximately 23° C.

Root description: Thin root stretching to downward reaching as deep as 3 feet or deeper with sandy soil.

PLANT

Age of plant described: Approximately 90 days from rooted cutting.

Time of year: June 2014.

Growth habit: Creeping, creating a dense mat.

Planting description: Not in a pot, planted in the ground outside of greenhouse.

Height: 4-5 cm.

Plant spread: 150 cm diameter, maximum in a year.

Growth rate: Vigorous growing.

Branching characteristics: Dense.

Length of primary lateral branches: 75 cm.

Diameter of lateral branches: 150 cm.

Quantity of primary lateral branches: Many.

Characteristics of primary lateral branches:

- *Form*.—Round.
- *Diameter*.—0.5 cm.
- *Color*.—Near Yellow-Green 147A, mottled Brown 200B and Brown N200B and N200C.
- *Texture*.—Slightly scaly.
- *Strength*.—Very strong, difficult to break.

Internode length: 4-5 cm.

FOLIAGE

Leaf:

- *Arrangement*.—Opposite along the stem.
- *Average length*.—1.9 cm.
- *Average width*.—1.1 cm.
- *Shape of blade*.—Obovate.
- *Apex*.—Acute.
- *Base*.—Attenuate.
- *Margin*.—Crenate.
- *Texture of top surface*.—Glabrous.
- *Texture of bottom surface*.—Glabrous.
- *Aspect*.—Slightly upwardly cupped.
- *Color*.—Young foliage upper(front) Green RHS 137C. Young foliage under(back) side: Green RHS 137D. Mature foliage upper side: Green RHS 137C. Mature foliage under side: Green RHS 137D.
- *Venation*.—Type: Venation color upper side: Green RHS 139D. Venation color under side: Green RHS 139D.
- *Petiole*.—Leaves sessile.

FLOWER

Natural flowering season: May to September.

Days to flowering from rooted cutting: 1-2 months, depend on temperature and light conditions.

Inflorescence and flower type and habit: Terminal umbel.

Persistent or self-cleaning: Persistent.

Bud:

- *Shape*.—Oval.
- *Length*.—0.5 cm.
- *Diameter*.—0.3 cm.
- *Color*.—Near RHS Purple RHS 77.

Inflorescence:

- *Depth*.—2.5 cm.
- *Diameter*.—2.7 cm.
- *Average quantity of individual flowers per inflorescence*.—18.

Corolla:

- *Individual flower*.—Depth: 0.4 cm. Diameter: 0.3 cm. Petals/lobes: Number: 1. Length: 0.4 cm. Width: 0.3 cm. Shape: Tube, flaring open at very end. Apex: Blunt, shallow lobes. Base: Fused. Margin: Ruffled apex. Texture: Glabrous all surfaces.
- *Color*.—When opening: Upper surface: Near Purple RHS 76D. Lower surface: Near Purple RHS 76D. Fully opened: Upper surface: Near Violet-blue RHS 91D. Lower surface: Near Violet-blue RHS 91D.

Throat:

- *Color*.—Purple RHS 76C.
- *Texture*.—Glabrous.

Tube:

- *Interior tube color*.—Purple RHS 76D and Yellow RHS 11A.
- *Exterior tube color*.—Purple RHS 76D.
- *Texture*.—Glabrous.

Calyx:

- *Form*.—Fused into a tube.
- *Length*.—0.1 cm.
- *Diameter*.—0.1 cm.
- *Sepal texture*.—Glabrous.
- *Sepal color*.—Upper surface: Green RHS 137B. Lower surface: Green RHS 137B.
- *Fragrance*.—None.

Pedicels: Not present.

Peduncles:

- *Length*.—1.5 cm to 3.0 cm.
- *Diameter*.—0.05 cm.
- *Color*.—Green RHS 139C.
- *Texture*.—Glabrous.

REPRODUCTIVE ORGANS

Stamens:
*Number* (*per flower*).—4.
*Filament length.*—0.05 cm.
*Anthers*.—Shape: Linear. Length: 0.05 cm. Color: Yellow RHS 11B.
Pollen:
*Color*.—Yellow RHS 11B.
*Amount*.—Very little.
Pistils:
*Quantity per flower.*—1. Minute, not measurable.

OTHER CHARACTERISTICS

Seeds and fruits: Not observed.
Disease/pest resistance: Excellent resistance to common disease and pests of *Lippia nodiflora.* New variety has better resistance to disease under humid and hot conditions than parents.
Temperature tolerance: Plant of the new hybrid have shown excellent resistance to high and low temperature extremes, having been grown successfully under temperature conditions ranging from a gentle frost outdoors, just below 0 degrees Celsius, to 50 degrees Celsius in an uncontrolled greenhouse.
Physical durability: New variety has excellent tolerance to be foot traffic.
Soil pH: New variety has excellent tolerance to a range of soil pH from 4.0-12.0.

What is claimed is:

1. A new and distinct cultivar of *Lippia* plant named 'ECOLOPIA1' as herein illustrated and described.

* * * * *